United States Patent
Neri et al.

(10) Patent No.: US 6,316,409 B1
(45) Date of Patent: Nov. 13, 2001

(54) MODIFIED LIGANDS OF CALCIUM-DEPENDENT BINDING PROTEINS

(75) Inventors: Dario Neri, Zurich (CH); Gregory Paul Winter, Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/142,356

(22) PCT Filed: Apr. 25, 1997

(86) PCT No.: PCT/GB97/01152
§ 371 Date: Mar. 3, 1999
§ 102(e) Date: Mar. 3, 1999

(87) PCT Pub. No.: WO97/40142
PCT Pub. Date: Oct. 30, 1997

(30) Foreign Application Priority Data

Apr. 25, 1996 (GB) .................................................. 9608510

(51) Int. Cl.⁷ .......................... A01N 37/18; A61K 38/00; C07K 14/00
(52) U.S. Cl. .............................. 514/12; 514/13; 514/14; 514/15; 530/300
(58) Field of Search ................................ 514/12, 13, 14, 514/15; 530/300

(56) References Cited

PUBLICATIONS

S. Montigiani et al., 1996, Alanine Substitutions in Calmodulin–Binding Peptides Result in Unexpected Affinity Enhancement, J. Mol. Biol., 258:6–13.

K. Torok et al., Nov. 1994, Mechanism of 2–chloro–(epsilon–amino–Lys75)–[6–[4–(N,N–diethylamino)phenyl]–1,3,5–triazin–4–yl] calmodulin Interactions with Smooth Muscle Myosin Light Chain Kinase and Derived Peptides, Biochemistry, 33:12807–20.

J.K. Krueger et al., Jul. 1995, Intrasteric Regulation of Myosin Light Chain Kinase, Journal of Biological Chemistry, 270:16848–53.

Ikura et al., 1992, Solution Structure of a Calmodulin–Target Peptide Complex by Multidimensional NMR, Science 256:632–638.

O'Neil et al., The Interaction of Calmodulin with Fluorescent and Photoreactive Model Peptides: Evidence for a Short Interdomain Separation, 1989, Proteins: Structure, Function, and Genetics, 6:284–293.

*Primary Examiner*—Christopher S. F. Low
*Assistant Examiner*—Stephen Tu
(74) *Attorney, Agent, or Firm*—Darby & Darby

(57) ABSTRACT

The present invention relates to ligands capable of binding a calcium dependent binding protein, that comprise an amino acid sequence corresponding to that of a wild type ligand for the calcium dependent binding protein with modification which results in enhanced affinity of the ligand for the calcium dependent binding protein.

19 Claims, 3 Drawing Sheets

SEQUENCE LISTING

```
<160> NUMBER OF SEQ ID NOS: 19

<210> SEQ ID NO 1
<211> LENGTH: 19
<212> TYPE: PRT
<213> ORGANISM: Artificial Sequence
<220> FEATURE:
<223> OTHER INFORMATION: skeletal myosin light chain kinase-calmodulin
      binding region

<400> SEQUENCE: 1

Arg Trp Lys Lys Asn Phe Ile Ala Val Ser Ala Ala Asn Arg Phe Lys
1               5                   10                  15

Lys Ile Ser

<210> SEQ ID NO 2
<211> LENGTH: 23
<212> TYPE: PRT
<213> ORGANISM: Artificial Sequence
<220> FEATURE:
<223> OTHER INFORMATION: calmodulin binding peptide-wild type

<400> SEQUENCE: 2

Cys Ala Ala Ala Arg Trp Lys Lys Asn Phe Ile Ala Val Ser Ala Ala
1               5                   10                  15

Asn Arg Phe Lys Lys Ile Ser
            20

<210> SEQ ID NO 3
<211> LENGTH: 23
<212> TYPE: PRT
<213> ORGANISM: Artificial Sequence
<220> FEATURE:
<223> OTHER INFORMATION: calmodulin binding peptide-R5A mutant

<400> SEQUENCE: 3

Cys Ala Ala Ala Ala Trp Lys Lys Asn Phe Ile Ala Val Ser Ala Ala
1               5                   10                  15

Asn Arg Phe Lys Lys Ile Ser
            20

<210> SEQ ID NO 4
<211> LENGTH: 23
<212> TYPE: PRT
<213> ORGANISM: Artificial Sequence
<220> FEATURE:
<223> OTHER INFORMATION: calmodulin binding peptide-W6A mutant

<400> SEQUENCE: 4

Cys Ala Ala Ala Arg Ala Lys Lys Asn Phe Ile Ala Val Ser Ala Ala
1               5                   10                  15
```

```
Asn Arg Phe Lys Lys Ile Ser
            20

<210> SEQ ID NO 5
<211> LENGTH: 23
<212> TYPE: PRT
<213> ORGANISM: Artificial Sequence
<220> FEATURE:
<223> OTHER INFORMATION: calmodulin binding peptide-K7A mutant

<400> SEQUENCE: 5

Cys Ala Ala Ala Arg Trp Ala Lys Asn Phe Ile Ala Val Ser Ala Ala
 1               5                  10                  15

Asn Arg Phe Lys Lys Ile Ser
            20

<210> SEQ ID NO 6
<211> LENGTH: 23
<212> TYPE: PRT
<213> ORGANISM: calmodulin Artificial Sequence
<220> FEATURE:
<223> OTHER INFORMATION: calmodulin binding peptide-K8A mutant

<400> SEQUENCE: 6

Cys Ala Ala Ala Arg Trp Lys Ala Asn Phe Ile Ala Val Ser Ala Ala
 1               5                  10                  15

Asn Arg Phe Lys Lys Ile Ser
            20

<210> SEQ ID NO 7
<211> LENGTH: 23
<212> TYPE: PRT
<213> ORGANISM: Artificial Sequence
<220> FEATURE:
<223> OTHER INFORMATION: calmodulin binding peptide-N9A mutant

<400> SEQUENCE: 7

Cys Ala Ala Ala Arg Trp Lys Lys Ala Phe Ile Ala Val Ser Ala Ala
 1               5                  10                  15

Asn Arg Phe Lys Lys Ile Ser
            20

<210> SEQ ID NO 8
<211> LENGTH: 23
<212> TYPE: PRT
<213> ORGANISM: Artificial Sequence
<220> FEATURE:
<223> OTHER INFORMATION: calmodulin binding peptide-F10A mutant

<400> SEQUENCE: 8

Cys Ala Ala Ala Arg Trp Lys Lys Asn Ala Ile Ala Val Ser Ala Ala
 1               5                  10                  15

Asn Arg Phe Lys Lys Ile Ser
            20

<210> SEQ ID NO 9
<211> LENGTH: 23
<212> TYPE: PRT
<213> ORGANISM: Artificial Sequence
<220> FEATURE:
<223> OTHER INFORMATION: calmodulin binding peptide-I11A mutant

<400> SEQUENCE: 9

Cys Ala Ala Ala Arg Trp Lys Lys Asn Phe Ala Ala Val Ser Ala Ala
```

```
                    1               5              10              15

Asn Arg Phe Lys Lys Ile Ser
                20

<210> SEQ ID NO 10
<211> LEN

```
Cys Ala Ala Ala Arg Trp Lys Lys Asn Phe Ile Ala Val Ser Ala Ala
1               5                   10                  15

Asn Arg Ala Lys Lys Ile Ser
            20
```

```
<210> SEQ ID NO 15
<211> LENGTH: 23
<212> TYPE: PRT
<213> ORGANISM: Artificial Sequence
<220> FEATURE:
<223> OTHER INFORMATION: calmodulin binding peptide-K20A mutant

<400> SEQUENCE: 15
```

```
Cys Ala Ala Ala Arg Trp Lys Lys Asn Phe Ile Ala Val Ser Ala Ala
1               5                   10                  15

Asn Arg Phe Ala Lys Ile Ser
            20
```

```
<210> SEQ ID NO 16
<211> LENGTH: 23
<212> TYPE: PRT
<213> ORGANISM: Artificial Sequence
<220> FEATURE:
<223> OTHER INFORMATION: calmodulin binding peptide-K21A mutant

<400> SEQUENCE: 16
```

```
Cys Ala Ala Ala Arg Trp Lys Lys Asn Phe Ile Ala Val Ser Ala Ala
1               5                   10                  15

Asn Arg Phe Lys Ala Ile Ser
            20
```

```
<210> SEQ ID NO 17
<211> LENGTH: 23
<212> TYPE: PRT
<213> ORGANISM: Artificial Sequence
<220> FEATURE:
<223> OTHER INFORMATION: calmodulin binding peptide-I22A mutant

<400> SEQUENCE: 17
```

```
Cys Ala Ala Ala Arg Trp Lys Lys Asn Phe Ile Ala Val Ser Ala Ala
1               5                   10                  15

Asn Arg Phe Lys Lys Ala Ser
            20
```

```
<210> SEQ ID NO 18
<211> LENGTH: 23
<212> TYPE: PRT
<213> ORGANISM: Artificial Sequence
<220> FEATURE:
<223> OTHER INFORMATION: calmodulin binding peptide-S23A mutant

<400> SEQUENCE: 18
```

```
Cys Ala Ala Ala Arg Trp Lys Lys Asn Phe Ile Ala Val Ser Ala Ala
1               5                   10                  15

Asn Arg Phe Lys Lys Ile Ala
            20
```

```
<210> SEQ ID NO 19
<211> LENGTH: 23
<212> TYPE: PRT
<213> ORGANISM: Artificial Sequence
<220> FEATURE:
<223> OTHER INFORMATION: calmodulin binding peptide-multiple mutations

<400> SEQUENCE: 19
```

-continued

```
Cys Ala Ala Ala Arg Trp Lys Lys Ala Phe Ile Ala Val Ala Ala Ala
 1               5                  10                  15

Asn Arg Phe Ala Lys Ile Ala
            20
```

MODIFIED LIGANDS OF CALCIUM-DEPENDENT BINDING PROTEINS

INTRODUCTION

Figure 1:
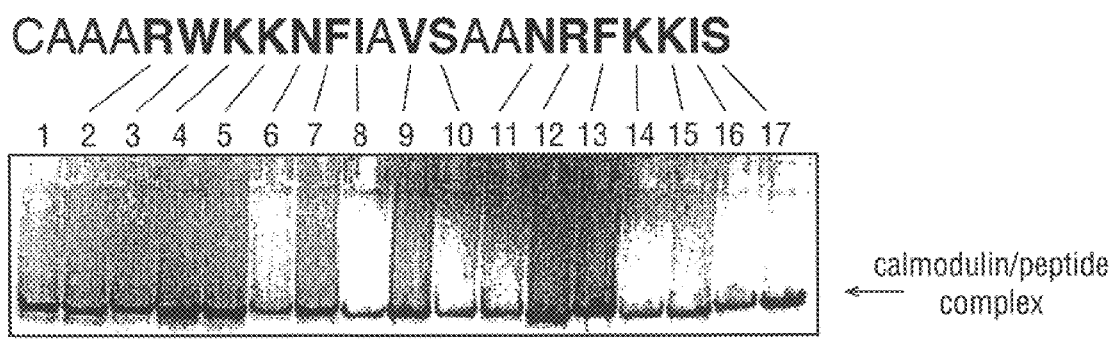

The present invention relates to targeting, detection, immobilization, and purification of molecules using binding pairs. In particular, it relates to the use of calcium dependent binding proteins and ligands thereof. The present invention provides ligands that possess improved affinity for calcium-dependent binding proteins. The binding pairs of the present invention provide an attractive alternative to currently available binding pair systems utilised in biological procedures.

BACKGROUND TO THE INVENTION

The term "binding pair" refers to two molecules that bind each other with high affinity. Many binding pair systems presently exist for the purification and targeting of tagged compounds. The most widely-used system at present is the biotin-streptavidin binding pair that has also been applied to in vivo tumour targeting methods (Paganelli et al., 1991). In addition, recombinant fusion proteins expressing the myc or Flag tags have been isolated and purified using antibodies directed against these tags (Munro and Pelham, 1986; Hopp et al., 1988). Poly-his peptide tails have been genetically fused to recombinant proteins and purified on nickel-coated agarose or using affinity columns (Skerra et al., 1991). The streptavidin-binding strep tag (Schmidt and Skerra, 1993) has been used in similar applications.

However, the application of each of the above examples is restricted. Techniques such as affinity purification require a specific yet low affinity interaction so as not to impair the function of the recombinant protein with a harsh elution protocol. Conversely, targeting and specific immobilization both require high affinity binding of the tag with a long half-life of interaction of the binding pair. The systems described in the prior art that employ binding pairs do not possess this flexibility, and thus are not universally applicable.

Calmodulin is a calcium dependent binding protein that regulates a wide range of enzymes, and plays a key role in intracellular signal transduction. It is also one of the few examples of a small protein capable of binding ligands with a high affinity.

Due to their small size, calmodulin-ligand compelexes have been used as convenient models for the study of protein association and dissociation. Since the elucidation of three-dimensional structures of calmodulin in complex with high affinity ligand substrates, this system has been amenable to the study of the mechanisms by which proteins recognise one another in high affinity interactions.

Pending patent application WO95/12672 discloses the use of binding pairs comprising calmodulin and calmodulin ligands for the detection, immobilization, targeting and purification of recombinant polypeptides. This system is attractive since the binding interaction can be modified through changes in calcium concentration that can easily be controlled through the use of calcium chelators. This greatly broadens the applicability of binding pairs as experimental and therapeutic tools.

Stoko-Hahn et al., (1992) have made a fusion of a calmodulin binding ligand tag derived from the C terminus of rabbit skeletal muscle myosin light chain kinase (sMLCK), and a recombinant protein. They have used this in purification strategies on an affinity support. In the presence of high levels of calcium, this system displays a specific high affinity interaction, the dissociation constant for the binding pair being of the order of 3 nM. The addition of EGTA (a calcium chelator) lowers the affinity of the interaction, allowing a very mild elution protocol, and meaning that denaturation or disruption of the native protein structure is unlikely. However, although the affinity of calmodulin towards calmodulin ligands is high, it is not sufficiently high for many targeting, immobilisation and particularly therapeutic applications.

For many therapeutic applications, sub nanomolar or picomolar dissociation constants, high association rate constants and extremely low dissociation rate constants are necessary to ensure efficient targeting of the complex and a sufficiently long half-life of the binding interaction. The biotin-streptavidin binding pair is widely used both experimentally and therapeutically for the targeting, purification and immobilization of proteins. The main attraction of this system lies in the high affinity of interaction ($K_d = 10^{-15}$ M) of the binding pair.

However, a significant disadvantage of using this binding pair is the immunogenicity of streptavidin in the human body. This greatly limits the utility of this system for therapeutic applications. There is thus a great need for an experimentally malleable binding pair system that possesses both a high affinity interaction and low immunogenicity.

DESCRIPTION OF THE INVENTION

According to the present invention, there is provided a ligand capable of binding a calcium dependent binding protein comprising an amino acid sequence corresponding to that of a wild type ligand for the calcium dependent binding protein, with a modification which results in enhanced affinity of the ligand for the calcium dependent binding protein.

By wild type ligand is meant a naturally-occurring ligand capable of binding a calcium dependent binding protein. All ligands as defined by the present invention are peptides that comprise a modification of the binding domain of naturally-occurring peptide ligands that interact with calcium dependent binding proteins.

Examples of wild type ligands from which suitable ligands may be derived are skeletal myosin light chain kinase, smooth muscle myosin light chain kinase, mastoparan, melittin, AC-28 and NO-30, all of which exhibit high affinity binding to calmodulin. Preferably, the ligand of the present invention comprises a modified skeletal myosin light chain kinase ligand.

The said modification may consist of a substitution, insertion, or deletion of one or more amino acids in the wild type ligand that results in improved affinity of the ligand for the calcium dependent binding protein. The ligand of the present invention may comprise up to 20, preferably up to 10, more preferably up to 5 modifications to the amino acid sequence of the wild type ligand.

By insertion and deletion is meant the introduction or omission respectively of one or more amino acids, to lengthen or shorten the amino acid sequence of the wild type ligand, and thus modify its affinity for the calcium dependent binding protein. Preferably the modification comprises a substitution of one or more amino acids in the wild type ligand.

A substitution comprises the replacement of a naturally-occurring amino acid in the wild type peptide sequence for a surrogate residue. The preferred surrogate residue is alanine or valine. Both these amino acids are hydrophobic with relatively innocuous side chains, and both are thus ideal for substitution into a helical peptide with minimal perturbation of the peptide structure. Fully worked examples describing the production, identification and manipulation of such molecules are disclosed herein. Preferably the surrogate residue is alanine.

Individual alanine residues have previously been inserted in the sequence of proteins. Clackson and Wells, (1995) recently reported the systematic replacement of contact residues in the sequence of the human growth hormone receptor (hGHbp). This "alanine scanning" technique identified the residues involved in the binding interaction through quantification of the decrease in binding affinities exhibited by these mutant proteins.

Barstar, a physiological inhibitor of barnase (the extracellular RNase in *Bacillus amylolique-faciens*), has also been subjected to such experimental manipulation. The very high association rate constant possessed by the barnase-barstar complex ($3.8 \times 10^9$ $s^{-1}M^{-1}$) is due to four acidic sidechain amino acid residues. When these were all individually mutated to alanine, this caused a decrease in the association rate constant. Concomitantly, a slight increase in the stability of barstar was seen, and it has therefore been hypothesized that proteins evolve primarily to optimize their function rather than their stability (Schrieber et al., 1994).

Surprisingly, the modified ligands of the present invention exhibit increased binding affinities and association constants. It seems that ligands capable of binding calcium dependent binding proteins have evolved to perform their biological function by achieving sufficiently high binding affinity, yet have failed to maximise binding affinity.

Multiple amino acid substitutions are also claimed in the present invention, and described herein. The combination of individual single amino acid substitutions can give a cumulative effect, leading to a much enhanced affinity of the ligand for the calcium dependent binding protein.

By calcium dependent binding protein it is meant a protein capable of binding a ligand wherein the dissociation constant for the ligand is reduced in the presence of calcium ions, that is, binding is much stronger in the presence of calcium ions.

The ligand of the present invention is suitable for many biotechnological applications, for example for protein purification and detection, conditional formation of bifunctional (macro)molecules, microscopy, FACS analysis, protein immobilisation on microsensor chips and tumour targeting. For many of these applications it is desirable for the calcium dependent binding protein-peptide ligand binding pair to have a very high affinity, with a fast on-rate of association, and a very slow off-rate (ie. dissociation rate constant).

For the applications described herein, it is preferred that calcium dependent reduction in binding affinity is at least ten-fold where the binding protein has one tenth of its calcium ion sites occupied. Preferably, the dissociation constant is greater than 10 nM at a pH of between 6 and 9 at 20° C., and 10 nM or less in the presence of 50 µM calcium ions, most preferably 1 nM or less. For some calcium dependent binding proteins, other analogous ions may replace calcium, for example strontium.

The preferred calcium dependent binding protein is calmodulin. This protein is relatively small (148 residues) and is thus suitable for use as one member of a binding pair. Hybrid recombinant proteins of calmodulin and another protein may be easily generated by genetic fusions; the use of a small protein as a tag reduces the risk of perturbing the protein structure of the fusion partner, and also reduces the chance of abrogating the function of that partner through steric hindrance.

It will be understood that other calcium-dependent binding proteins such as troponin C, calcineurin, parvalbumin and oncomodulin may also be employed in the present invention.

Several proteins, peptides, or organic compounds bind to calmodulin with high affinity (with a nM or sub nM dissociation constant). Indeed, three-dimensional structures are available of calmodulin and peptide ligands (Ikura et al., 1992; Meador et al., 1992, 1993). The NMR structure of the complex between calmodulin and a 26 amino acid peptide derived from skeletal myosin light chain kinase (sMLCK) has shown that only the central 19-mer sequence RWKKN-FIAVSAANRFKKIS contacts (SEQ ID NO: 1) calmodulin (Ikura et al., 1992). In the present invention, the preferred wild type peptide ligand comprises a modification of this sequence, as described further herein.

It is preferred that the ligand of the present invention shows a reduction in $K_d$ by a factor of at least 10, preferably by a factor of at least 100, more preferably by a factor of at least 1000, over the wild type ligand, wherein $$K_d = k_{off}/k_{on}$$

where $k_{off}$=the kinetic dissociation constant of the reaction and
$k_{on}$=the kinetic association constant of the reaction The decrease in dissociation constant may be derived from modification of either the $k_{off}$ or $k_{on}$ values, or through a combination of modifications in both kinetic values. Preferably, the improvement in binding affinity reflected by a lowering of the dissociation constant is dominated by a lowered $k_{off}$ value, by a factor of at least 10, more preferably at least 100 and most preferably by a factor of at least 1000. The binding affinity is also reflected in the half-life ($t_{1/2}$) of interaction, wherein $$t_{1/2} = 1/k_{off}.$$

Preferably the half-life of the interaction is at least 15 minutes, more preferably at least one hour.

Peptides 6, 10, and 17 (SEQ ID NOS: 7, 11 and 18) in the accompanying Table 1 show the greatest improvement in $K_d$ over the wild type peptide. In particular, peptide 6 (SEQ ID NO:1) is the ligand of choice.

According to a further aspect of the present invention there is provided a method of enhancing the binding affinity of a wild type calcium dependent binding ligand comprising the step of modifying the amino acid sequence of the wild type calcium dependent binding ligand.

The ligands of the present invention may be synthesized by conventional peptide synthetic techniques including solid phase oligopeptide synthesis and recombinant DNA techniques.

Robotic multi-well peptide synthesizers allow the production of many different peptides comprising multiple amino acid substitutions in 1–2 days. Parallel methods of peptide deprotection, cleavage and fluorescent labelling with multi-well devices, allow rapid analysis of the peptides generated. The native gel electrophoresis method used herein for the measurement of kinetic dissociation constants by competition experiments can also be used in parallel with peptide production, using multiple multi-well gels.

In addition, libraries of peptides can be designed and expressed on the surface of filamentous phage by recombinant DNA techniques (Smith et al., 1985). Suitable stringent selection/amplification and screening techniques (for example parallel fluorescent native gel electrophoresis) can be used to identify improved ligands.

According to a further aspect of the present invention, there is provided a binding pair comprising a calcium dependent binding protein and a ligand according to the present invention.

According to the present invention there is provided use of a ligand according to the present invention in conjunction with a calcium dependent binding protein as a binding pair. The calcium dependent binding protein-ligand binding pair of the present invention may be employed in any application requiring a high affinity binding pair. Modification of the binding affinity according to the present invention allows the binding affinity of the binding pair to be tailored to the requirements of the specific application.

According to a further aspect of the present invention, the ligand of the present invention may be linked with another moiety. For example, co-pending United Kingdom patent application "Isolation of enzymes" filed in the name of the Medical Research Council on Apr. 25, 1996 discloses the use of calmodulin linked to an enzyme. In addition, calmodulin ligands are linked to substrate for the particular reaction catalysed by the enzyme. Following binding of the calmodulin-enzyme moiety and the ligand-substrate moiety and conversion of substrate to product by the enzyme, the product remains bound to the enzyme (via the calmodulin-calmodulin ligand binding pair) after the product has dissociated from the active site. This allows the isolation of active enzyme from an enzyme library, by selection of the product of the enzymatic reaction. If the enzyme is linked to the DNA encoding it (for example by being displayed on the surface of phage), isolation of the encoding DNA species is also possible.

The present invention may be used to increase the binding affinity and thus half-life of the interaction of the calmodulin-calmodulin ligand binding pair used in the above-mentioned procedure. This is advantageous particularly in the case of enzymes that possess a slow rate of reaction. For these enzymes, the calmodulin-ligand interaction must exhibit a sufficiently long half-life to allow the completion of the enzymatic reaction, so as not to allow dissociation of substrate from the enzyme. The use of the ligands of the present invention will broaden the application of this "enzyme selection" technology.

The linked moiety may be a protein. Preferably the ligand-protein fusion is produced from a gene fusion. Nucleic acid encoding such fusions forms a further aspect of the present invention. Host cells transfected with an expression vector encoding such a recombinant fusion protein may be grown in culture and used for the production of such molecules. The ligand may then be used for the isolation and purification of the recombinant molecules, by processes such as affinity chromatography or ion exchange chromatography on (calmodulin) antagonist columns. Elution may make use of a calcium chelator to lower the affinity of calmodulin for the ligands.

Alternatively, the linked moiety may be appended to the ligand non-covalently, or by chemical modification. Chemical modification includes, for example, linking reactive functional groups such as thiol, hydroxy, amino, carboxy, or aryl groups present in the ligand to reactive functional groups present in the linked moiety. For instance, a cysteine group can be incorporated at the C-terminus of the ligand, and a protein coupled using a heterobifunctional crosslinker such as SPDP (N-succinimidyl 3 (2-pyridyldithio) propoinate). For non-covalent linkage, peptides favouring formation of dimers (such as leucine zippers or the protein binding domains on Jun and Fos) may be appended to the peptide, and to the recombinant protein. The complex thus forms on mixing of the protein and ligand.

The linked moiety may also be a label. The label may be fluorescent (eg. fluorescein), an antibody label, or a radio-label. This permits detection and isolation of recombinant fusion proteins comprising a calcium dependent binding protein by methods such as fluorescence activated cell sorting (FACS), confocal fluorescence microscopy or blotting. Other highly sensitive methods for detection of calcium dependent binding proteins may be developed, for example by $Tb^{3+}$ luminescence after replacing $Ca^{2+}$ ions with $Tb^{3+}$ ions as recently described for oncomodulin. (Clark et al., 1993). Through the use of a labelled ligand of the present invention, measurements of binding affinity may also be made using a band shift assay as described in co-pending patent application WO95/12672.

A variety of techniques are under development to improve the efficacy and tumour cell specificity of cancer treatment. Chemotherapy has proven to display a low therapeutic index, which causes unacceptable damage to normal organs, and limits the dose of drugs that can safely be administered.

For many years, antibodies have been investigated as means to deliver cytotoxic proteins to kill target cells, and indeed, the majority of research is at present directed towards antibody-directed therapy. The cell specificity of antibodies or their immunoreactive fragments can be harnessed to deliver drugs, radioisotopes, protein cytotoxins, effector cells of the immune system, and even enzymes for targeted prodrug activation. However, despite outstanding results in vitro and in vivo, considerable problems remain, such as the immunogenicity of the molecule(s) and systemic toxicity, that must be resolved before effective clinical trial results may be obtained.

One method that attempts to resolve the systemic toxicity associated with direct antibody-mediated delivery is the pre-targeted delivery of therapeutic agents using streptavidin and biotin based conjugates. The target-specific agent (normally an antibody) is fused to streptavidin and administered to a mammal. After a relevant localisation time, a second conjugate is administered that comprise biotin linked to a toxin or radioisotope. Thus, the targeting ratio and/or active dose of the cytotoxic agent is increased at the target organ. In addition, exposure to non-target tissues (especially bone marrow) is reduced, and the delivery and efficient utilisation of larger doses becomes possible.

Non-targeted label is efficiently excreted from the body through the kidneys. However, the degree of efficiency of this therapy is markedly reduced by the immunogenicity of streptavidin, and thus also of its conjugates. This necessitates the simultaneous administration of an immunosuppressant, an inefficient measure that raises the degree of trauma associated with the therapy. There is thus a need for an analogous system comprising a binding pair that exhibits both high binding affinity and low immunogenicity in the mammalian body.

Calcium dependent binding proteins such as calmodulin and peptide ligands therefor are thus ideal candidates for such a therapeutic regime due to their natural occurrence in the mammalian body, and thus low immunogenicity (VanEldik and Lucas, 1987). In addition, it has been shown that calmodulin is not toxic, does not accumulate selectively in any organ, and is secreted rapidly in the urine. However, the interaction of calmodulin with naturally-occurring peptide ligands is of too low affinity for effective use in this application.

The present invention provides a peptide ligand of improved affinity for calmodulin. Thus, another embodiment is a molecule comprising the ligand of the present invention linked to a toxin. This toxin may comprise drugs, a radioisotope, a protein cytotoxin, an effector cell of the immune system, an enzyme for prodrug activation, a Pseudomonas toxin, tumour necrosis factor alpha, or another toxin with a chemotherapeutic action. It will be understood that any suitable toxin may be used as a fusion partner in the present invention for pretargeted delivery of therapeutic agents.

The same technique, only involving the fusion of the ligand to a radiolabel, may be used in immunoscintography for the diagnosis and imaging of tumours.

In addition to use of the ligand as the labelled or conjugated molecule in the embodiments described above, the format may be reversed so that the moiety fused to the toxin or label is the calcium dependent binding protein molecule, and the entity to which this is targeted is the peptide of the present invention. All the concepts described above are thus innately reversible.

In addition, fragments of these ligands and calcium dependent binding protein molecules that retain binding activity may be used, as may their derivatives. The term "derivative" encompasses amino acid variants containing deletions, substitutions, or insertions, that lead to altered physical or chemical molecular properties.

The strong binding interactions between calcium dependent binding proteins and peptide ligands may also provide a means of creating dimers or multimers. Dimeric peptide ligands could be used to dimerise recombinant calcium dependent binding protein fusion molecules. In the same way, multimeric peptide ligands would be capable of producing multimers. This would be particularly applicable in the case of calmodulin-antibody multimers formed using such ligands that could be used to increase the efficiency of tumour targeting, and thus the efficacy of the immune response.

Various aspects and embodiments of the present invention are illustrated in the following examples with reference to the figures. Further aspects and embodiments of the present invention will be apparent to those skilled in the art.

All documents mentioned in the text are incorporated by reference.

FIG. 1 illustrates detection of the complex between calmodulin and fluorescein-labelled peptides by native polyacrylamide gel electrophoresis.

The number of the lane corresponds to the peptide number. The position of the substitution is indicated with a line connecting the gel lane and the amino acid sequence.

Figure 2:
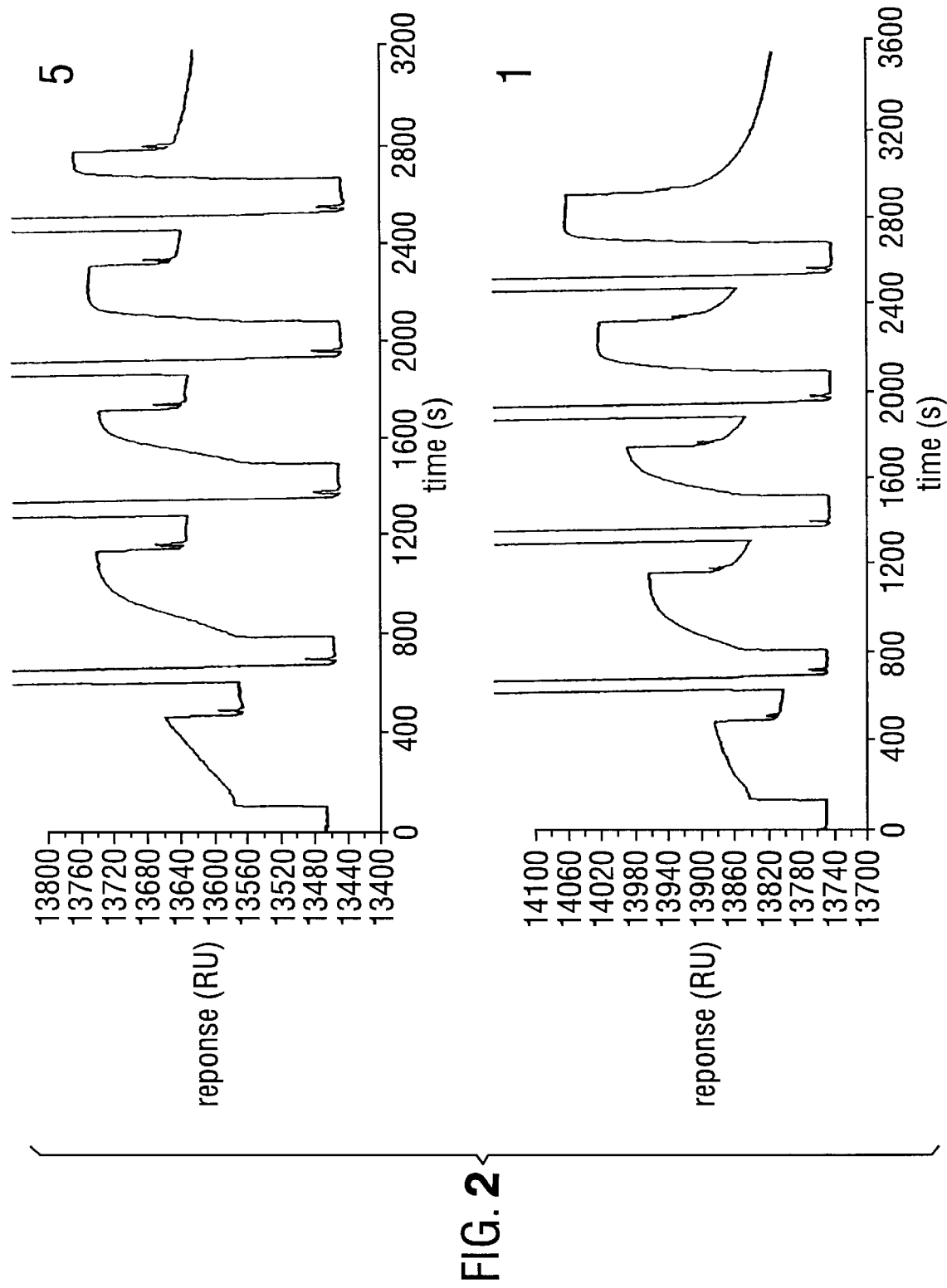

FIG. 2 illustrates typical sensograms as calmodulin binding to peptides 1–17 (SEQ ID NOS:2–18).

Here the results are shown for peptides 1 and 5 (SEQ ID NOS: 2 and 6).

Figure 3:
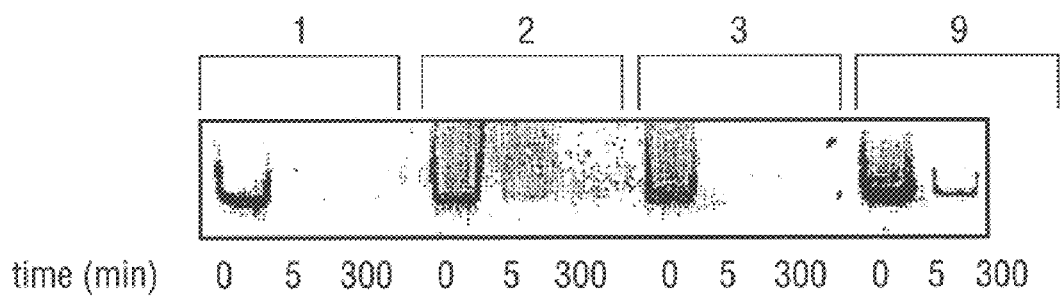
Figure 3:
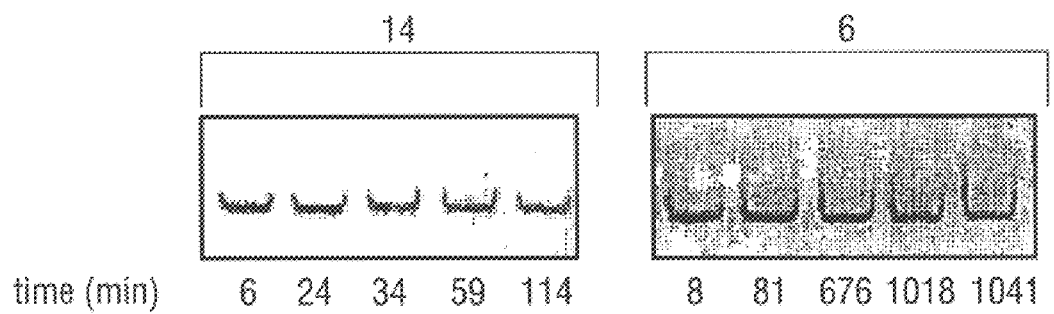

FIG. 3 illustrates competition experiments for the measurement of $k_{off}$ constants for peptides 1–17 (SEQ ID NOS: 2–18) towards calmodulin.

Here the results of the competitions are shown for peptides 1, 2, 3, 6, 9 and 14 (SEQ ID NOS: 2,3,4,7,10 and 15). Incubation times (in minutes) are indicated under the lanes.

The following examples are provided by way of example only. It will be appreciated that modification of detail may be made without departing from the scope of the invention.

EXAMPLES

Example 1

Design and Synthesis of Peptides

It has previously been shown that in skeletal myosin light chain kinase, only the central 19-mer sequence RWKKN-FIAVSAANRFKKIS (SEQ ID NO:1) contacts calmodulin. A modification of this peptide was therefore chosen as a model for the design of peptides directed against the calmodulin binding site.

Peptide 1 contains the wild type sequence and was designed using an N terminal cysteine to act as a target for site-specific peptide functionalisation with thiol-specific reagents (such as iodoacetamido fluorescein or biotin derivatives). The following three alanines are spacers, and at the C terminal, an amide group is provided. The sequence of this peptide is thus CAAA-RWKKNFIAVSAANRFKKIS-CONH$_2$ (SEQ ID NO: 2). 16 further peptides were synthesized corresponding to alanine mutations of all the non-alanine residues in the calmodulin recognition sequence (SEQ ID NOS:3–18). The sequences of these peptides are shown in Table 1, which also provides data on the kinetic analysis of the interaction between calmodulin and calmodulin-binding peptides by individual amino acid replacement to analine.

Peptides were made on a solid phase using a multiple peptide synthesizer (Multisyn Tech, Bochum, Germany) employing Fmoc/t-butyl protecting groups. The Fmoc group was cleaved by 40% (v/v) piperidine in dimethylformamide and successive amino acids were added as N-hydroxybenzotriazole esters. The peptides were deprotected and cleaved from the resin using 93% trifluoroacetic acid; 3% ethanedithiol; 2% anisole; 2% water. Peptides were analyzed by HPLC using a Vydac C18 column (10 $\mu$M, 100×250 mm) and by amino acid analysis (PICO TAG, Waters, Milford, Mass.).

Example 2

Detection of the Complex Between Calmodulin and Fluorescein-Labelled Peptides by Native Polyacrylamide Gel Electrophoresis (PAGE)

Complexes between calmodulin from bovine brain (1 $\mu$M, Sigma) and fluorescein-labelled sMLCK-derived peptides (as described in Table 1 (SEQ ID NOS:2–18)) were prepared in gel buffer (25% gel mix [4 g sucrose+1 mg bromophenol blue in water to give a 10 ml solution]+75% TBSC [50 mM TRIS pH 7.4, 100 nM NaCl+50 $\mu$M CaCl$_2$)] and run on a 15% native PAGE gel (5 ml 30% acrylamide-bisacrylamide solution+4.5 ml water+0.5 ml 3M Tris, pH 8.8, +1 $\mu$l 1M CaCl$_2$ polymerised with 30 $\mu$l 25% ammonium persulphate and 9 $\mu$l TEMED) using 14.4 g/l glycine+3 g/l Tris-base+0.1 mM CaCl$_2$ as running buffer. Peptides were labelled either with iodoacetamido fluorescein (Molecular Probes) or with iodoacetamido-LC-biotin (Pierce) essentially as previously described by Neri et al., (1995). In these conditions, the fluorescence of the positively-charged labelled peptides can be detected only if they form a stable complex with calmodulin.

FIG. 1 shows that all the synthesized peptides (SEQ ID NOS:2–18) bind to calmodulin in native PAGE gels, indicating that single alanine substitutions have no severely deleterious effect on calmodulin binding. The number of the lane corresponds to the peptide number. The position of the substitution is indicated with a line connecting the gel lane and the amino acid sequence. No fluorescent band can be detected with non-correlated labelled peptides (data not shown). The gels were imaged with the chemiluminescence analyzer LUANA (Neri et al., 1996).

Example 3

Measurement of the Isomerization, Association and Dissociation Kinetics of Calmodulin-Binding Peptides It has been shown by Török and Trentham (1994) that smooth muscle MLCK-derived peptides bind to calmodulin with a biphasic kinetic according to the scheme:

in which P is the peptide, C is calmodulin, P-C is the first complex formed on association of P and C, which then undergoes a conformational isomerisation to P-C*.

Stopped-flow analysis of the calmodulin binding to the sMLCK-derived peptides of the present invention shows a biphasic binding kinetic (data not shown). For a kinetic and thermodynamic characterisation of the binding of the peptides of the present invention to bovine brain calmodulin, we have measured the kinetic isomerisation, association, and dissociation constants from which dissociation constants can be derived. This allows assessment of those mutations that have resulted in increased affinity towards calmodulin.

used to determine $k_{on}$ and $k_{off}$ constants. Biotinylated peptides 1–17 were bound to commercially available streptavidin-coated microsensor chips (Pharmacia Biosensor), in order to achieve a surface capacity of 100–200 surface plasmon resonance units of calmodulin bound. Different concentrations of calmodulin (5, 10, 20, 50 and 100 nM in the order of FIG. 2) were injected and allowed to associate with the peptides. Regeneration of the surface was achieved by injection of 5 μl TBS+15 nM EDTA which dissociates the calmodulin-peptide complex. FIG. 2 shows sensograms of peptides 1 and 5 (SEQ ID NO: 2 and 6), in which the difference in $k_{on}$ and $k_{off}$ between the two peptides can be visually appreciated. $k_{on}$ and $k_{off}$ constants were obtained from the sensograms using the BIAevaluation software version 2.1 according to the manufacturers instructions (Pharmacia Biosensor). The results of the BIAcore measurements are listed in Table 1.

TABLE 1

KINETIC ANALYSIS OF THE INTERACTION BETWEEN
CALMODULIN AND CALMODULIN-BINDING PEPTIDES
BY INDIVIDUAL AMINOACID REPLACEMENT TO ALANINE

Peptide Sequence:
```
0           1           2
1------------ 0------------ 0---
CAAARWKKNFIAVSAANRFKKIS
```
(boldface: single-point mutations to alanine in individual peptides)

| pept. | mutation | $k_{isom.}$ (s$^{-1}$)[A] | $k_{on}$ (s$^{-1}$M$^{-1}$)[B] | $k_{off}$ (s$^{-1}$)[C] | $k_{off}$ (s$^{-1}$)[B] | $K_d$ (M)[D] |
|---|---|---|---|---|---|---|
| 1 | wt | 1.9 (10.7) × 10$^{-1}$ | 6.5 (11.6) × 10$^5$ | ≥1 × 10$^{-3}$ | 2.4 (±0.6) × 10$^{-3}$ | 3.7 (±1.8) × 10$^{-9}$ |
| 2 | R5-->A | 1.2 (10.5) × 10$^{-1}$ | 3.0 (10.7) × 10$^6$ | ≥1 × 10$^{-3}$ | 1.5 (±0.4) × 10$^{-3}$ | 5.0 (±2.5) × 10$^{-10}$ |
| 3 | W6-->A | N.D. | 3.2 (10.8) × 10$^6$ | ≥1 × 10$^{-3}$ | 5.0 (±1.2) × 10$^{-3}$ | 1.6 (±0.8) × 10$^{-9}$ |
| 4 | K7-->A | 2.4 (10.6) × 10$^{-1}$ | 1.3 (10.3) × 10$^6$ | ≥1 × 10$^{-3}$ | 3.0 (±0.7) × 10$^{-3}$ | 2.3 (±1.1) × 10$^{-9}$ |
| 5 | K8-->A | 7.4 (11.0) × 10$^{-2}$ | 1.1 (10.3) × 10$^6$ | 2.1 (±1.0) × 10$^{-4}$ | 2.9 (±0.7) × 10$^{-4}$ | 2.6 (±1.3) × 10$^{-10}$ |
| 6 | N9-->A | 1.8 (10.9) × 10$^{-1}$ | 9.8 (12.5) × 10$^5$ | 2.2 (±1.1) × 10$^{-6}$ | ≥1 × 10$^{-4}$ | 2.2 (±1.4) × 10$^{-12}$ |
| 7 | F10-->A | 2.5 (10.7) × 10$^{-1}$ | 9.0 (12.2) × 10$^5$ | 6.0 (±3.0) × 10$^{-4}$ | 3.9 (±1.0) × 10$^{-4}$ | 4.3 (±2.1) × 10$^{-10}$ |
| 8 | I11-->A | 1.1 (10.3) × 10$^{-1}$ | 9.2 (12.3) × 10$^5$ | 4.7 (±2.3) × 10$^{-4}$ | 2.3 (±0.6) × 10$^{-4}$ | 2.5 (±1.2) × 10$^{-10}$ |
| 9 | V13-->A | 1.5 (10.3) × 10$^{-1}$ | 8.6 (12.1) × 10$^5$ | ≥1 × 10$^{-3}$ | 1.2 (±0.3) × 10$^{-3}$ | 1.4 (±0.7) × 10$^{-9}$ |
| 10 | S14-->A | 2.1 (11.0) × 10$^{-1}$ | 1.1 (10.3) × 10$^6$ | 7.9 (±3.9) × 10$^{-5}$ | 1.0 (±0.2) × 10$^{-4}$ | 9.1 (±4.5) × 10$^{-11}$ |
| 11 | N17-->A | 2.8 (10.6) × 10$^{-2}$ | 8.3 (10.5) × 10$^5$ | 4.9 (±2.4) × 10$^{-4}$ | 3.5 (±0.9) × 10$^{-4}$ | 3.7 (±1.8) × 10$^{-10}$ |
| 12 | R18-->A | 1.7 (10.4) × 10$^{-1}$ | 1.6 (10.4) × 10$^6$ | 8.3 (±4.1) × 10$^{-4}$ | 4.1 (±1.0) × 10$^{-4}$ | 1.8 (±0.9) × 10$^{-10}$ |
| 13 | F19-->A | 1.8 (10.8) × 10$^{-1}$ | 9.3 (12.3) × 10$^5$ | ≥1 × 10$^{-3}$ | 8.4 (±2.1) × 10$^{-4}$ | 9.0 (±4.5) × 10$^{-10}$ |
| 14 | K20-->A | 1.6 (10.2) × 10$^{-1}$ | 2.5 (10.6) × 10$^6$ | 1.5 (±0.7) × 10$^{-4}$ | 1.4 (±0.4) × 10$^{-4}$ | 5.6 (±2.8) × 10$^{-11}$ |
| 15 | K21-->A | 1.2 (10.3) × 10$^{-1}$ | 1.1 (10.3) × 10$^6$ | 2.1 (±1.0) × 10$^{-4}$ | 2.2 (±0.5) × 10$^{-4}$ | 2.0 (±1.0) × 10$^{-10}$ |
| 16 | I22-->A | 8.7 (11.5) × 10$^{-2}$ | 8.1 (12.0) × 10$^5$ | 2.8 (±1.4) × 10$^{-4}$ | 3.1 (±0.8) × 10$^{-4}$ | 3.8 (±1.9) × 10$^{-10}$ |
| 17 | S23-->A | 1.3 (10.4) × 10$^{-1}$ | 8.2 (12.0) × 10$^5$ | 7.0 (±3.5) × 10$^{-5}$ | 1.3 (±0.3) × 10$^{-4}$ | 1.6 (±0.8) × 10$^{-10}$ |

Legend To Table 1:
A) $k_{isom.}$ (s$^{-1}$) measured by stopped-flow as described in FIG. 2
B) $k_{on}$ (s$^{-1}$M$^{-1}$) and $k_{off}$ (s$^{-1}$) measured by BIAcore as described in FIG. 2. Only a condition is reported for $k_{off}$ (s$^{-1}$)[B] of peptide 6. This is due to the fact that measurement of very slow dissociation constants by BIAcore is made difficult by rebinding effects and by baseline instability, particularly when, like in the present study, calcium ions are used and the microsensor chip is derivatised to low surface density.
C) $k_{off}$ (s$^{-1}$) values measured by competition as described in FIG. 2
D) $K_d$ (M) = $k_{off}$ (s$^{-1}$)[B]/$k_{on}$ (s$^{-1}$M$^{-1}$)[B], except for peptide 6 for which $K_d$ = $k_{off}$ (s$^{-1}$)[C]/$k_{on}$ (s$^{-1}$M$^{-1}$)[B]
N.D. = Not Determined $$k_{isom} = k_{+2} + k_{-2} \quad [1]$$

$$k_{on} = k_{+1} \quad [2]$$

$$k_{off} = k_{-1} \cdot k_{-2}/(k_{+2} + k_{-2}) \quad [3]$$

$$K_d = k_{off}/k_{on} \quad [4]$$

$k_{isom}$ constants have been measured by stopped-flow, detecting changes in tryptophan fluorescence for all the peptides except 3 (SEQ ID NO:4), in which the tryptophan is replaced by alanine. These values are shown in Table 1.

Real-time interaction analysis by surface plasmon resonance on a BIAcore instrument (Jönsson et al., 1991) was Kinetic association constants ($k_{on}$) of sMLCK-derived peptides 1–17 (SEQ ID NOS:2–18) are in the range 6.5× 10$^5$–3.2×10$^6$ s$^{-1}$M$^{-1}$, and are more than 100-fold lower than those of smooth muscle MLCK-derived peptides (Török and Trentham, 1994). The largest increase in $k_{on}$ with respect to the wild-type peptide 1 (SEQ ID NO:2) was observed for R5 (peptide 2 (SEQ ID NO:3)), W6 (peptide 3, SEQ ID NO:4) and K20 peptide (peptide 14 (SEQ ID NO:15)) mutations to alanine (4-5 fold increase; Table 1). Thus alanine mutations of two positively-charged amino acid residues (R5 and K20) are associated with increased on-rates.

Certain alanine mutations improve $k_{off}$ values up to 1 000-fold with respect to the wild-type peptide 1. (Table 1 (SEQ ID NO:2)). The largest improvements are observed for the replaced hydrophillic residues (N9, S14, S23), which are not stable in the hydrophobic environment of the calmodulin core. These correspond to peptides 6, 10, and 17 (SEQ ID NOS:7, 11 and 18).

Example 4

Determination of $k_{off}$ Constants by Competition Experiments

In order to obtain an independent experimental confirmation if the BIAcore results, $k_{off}$ constants for peptides 1–17 towards calmodulin were determined by competition experiments. 30 nM fluorescein-labelled peptide/calmodulin complexes in gel buffer were competed at room temperature for different times with 30-fold excess of unlabelled peptide. The resulting mixtures were run on native PAGE gels and imaged by LUANA as described above. The bands in the image obtained were integrated using the LUANA software (Neri et al., 1996) and the corresponding intersities plotted versus time and fitted with a single exponential, from which $k_{off}$ constants were derived. In order to normalise band intensities against pipetting errors, the samples contained 6 nM free fluorescein which ran with the front. The fluorescein bands were integrated and used to normalise the calmodulin/fluorescent peptide complex band intensity. The results of competitions for peptides 1, 2, 3, 6, 9, and 14 are shown in this FIG. 3. Incubation time in minutes is indicated under the lanes.

In the fast off-rate extreme, peptides 1, 2, 3 and 9 (SEQ ID NO:2,3,4, and 10) dissociated from calmodulin in a few minutes. Peptide 14 (SEQ ID NO:15) is representative of an intermediate off-rate, whereas 6 (SEQ ID NO:7) is hardly competed by an excess of unlabelled peptide after 1000 minutes. The volumes of the bands were plotted versus competition time and fitted to a single exponential, from which $k_{off}$ values were derived. The values are shown in Table 1.

The fastest competitions (peptides 1–4, 9 and 13, SEQ ID NOS:2–5,10, and 14) were over by the time the calmodulin/fluorescent peptide complex entered the gel (approximately 5–10 minutes from pipetting a molar excess of unlabelled peptide; FIG. 3), from which a condition on the off-rate constant $k_{off}>1\times10^{-3}$ s$^{-1}$ was derived. Even for these fast off-rates, complexes can be detected by native polyacrylamide gel electrophoresis because of the well known gel "cage effect" (Fried and Crothers, 1981; Garner and Revzin, 1981).

The $k_{off}$ values measured by competition and by BIAcore are in substantial agreement (Table 1). Small differences between the two sets of data may be due to the fact that competition experiments were performed in gel mix buffer (FIG. 3) rather than in TBS+50 μM CaCl$_2$.

Example 5

Construction of Further Mutations

Due to the enhanced binding affinity for Calmodulin shown by peptide 6 (SEQ ID NO:7) over all other tested peptides, further single point mutations of the asparagine residue 9 of the wild type peptide were constructed. The sequence of these peptides is shown in table 2, along with the $K_D$ values, measured according to the methods described in Example 3 and 4. Hydrophobic donor residues (valine, phenylalanine and leucine) were chosen because it was hypothesized that these residues would contribute to the stability of the hydrophobic environment in the calmodulin core.

All of the designed peptides possessed greater affinity for calmodulin than did the wild type sMLCK peptide, although none of the three showed greater affinity than peptide 6 (SEQ ID NO:7).

TABLE II

Kinetic analysis of the interaction between calmodulin and calmodulin-binding peptides by replacement of N9 to various hydrophobic residues.

| peptide | mutation | $K_{on}$ | $K_{off}$ | $K_D$ (M) |
| --- | --- | --- | --- | --- |
| wild type | wt | $6.1 \times 10^5$ | $5.9 \times 10^{-6}$ | $3.9 (\pm 1.8) \times 10^{-9}$ |
| a | N9→V | $8.5 \times 10^5$ | $3.5 \times 10^{-4}$ | $1 \times 10^{-9}$ |
| b | N9→F | $2.9 \times 10^5$ | $2.9 \times 10^{-5}$ | $1 \times 10^{-10}$ |
| c | N9→L | $1.1 \times 10^6$ | $2.3 \times 10^{-5}$ | $3 \times 10^{-11}$ |

Example 6

Construction of Multiple Mutations

The mutant peptides that exhibited the greatest improvement in affinity for calmodulin were peptides 6, 10 and 14 (SEQ ID NOS:7,11 and 15), corresponding to alanine substitutions at positions 9, 14 and 20 respectively. A multiple mutant was constructed in which these three residues were altered to alanine SEQ ID NO:19. The sequence was as shown below, with the replacement residues shown in bold:

CAAARWKKAFIAVAAANRFAKIA

Using the methods of examples 3 and 4, the dissociation constant of this peptide for calmodulin was found to be $1\times10^{-11}$ M ($k_{on}=6.1\times10^5$; $k_{off}=5.9\times10^{-6}$). The affinity of this peptide for calmodulin is therefore comparable to that of peptide 6. However, no synergistic effect was achieved by mutating all of the hydrophilic residues in the peptide.

REFERENCES

Clackson, T. and Wells, J. A. (1995). *Science* 267, 383–386.

Clark, I. D., MacManus, J. P., Banville, D. and Szabo, A. G. (1993) *Anal. Biochem*, 210, 1–6.

Fried, M. and Crothers, D. M. (1981) *Nucleic Acids Res.* 9, 6505–6525.

Garner, M. M. and Revzin, A. (1981) *Nucleic Acids Res.* 9, 3047–3060.

Hopp T. P., Prockett, K. S., Price, V. L., Libby, R. T., March, C. J., Cerretti, D. P., Urdal, D. L. and Conlon, P. J. (1988) *Bio/Technology* 9, 273–278.

Ikura, M., Clore, G. M., Gronenborn, A. M., Zhu, G., Klee, C. B., and Bax, A. (1992). *Science* 256, 632–638.

Jönsson, U., Fägerstam, L., Ivarsson, B., Johnsson, B., Karlsson, R., Lundh, K., Löfås, S., Persson, B., Roos, H., Rönnberg, I., Sjölander, S., Stenberg, E., Ståhlberg, Urbaniczky, C., Östlin, H. and Malmqvist, M. (1991) *BioTechniques* 11, 620–627.

Meador, W., Means, A. and Quiocho, F. (1992). *Science* 257, 1251–1257.

Meador, W., Means, A. and Quiocho, F. (1993). *Science* 262, 1718–1721.

Munro, S. and Pelham, H. R. B. (1986) *Cell* 46, 291–300.

Neri, D., de Lalla, C., Petrul, H., Neri, P. and Winter, G. (1995) *Bio/Technology* 13, 373–377.

Neri, D., Prospero, T., Petrul, H., Winter, G., Brown, M. and Vanderpant, L. (1996) *BioTechniques,* in press.

Paganelli, G., Magnani, P., Zito, F., Villa, E., Sudati, F., Lopalco, L., Rosetti, C., Malcovati, M., Chiolerio, F., Seccamani, E., Siccardi, A. G. and Fazio, F. (1991) *Cancer Res.* 51, 5960–5966.

Schmidt, T. G. M and Skerra, A. (1993) *Protein Eng.* 6, 109–122.

Schrieber, G., Buckle, A. M. and Fersht, A. (1994). *Structure* 2, 945–951.

Skerra, A. Pfitzinger, I. and Plückthun, A. (1991) *Bio/Technology* 6, 1204–1210

Smith, G. P. (1985) *Science* 228, 1315–1317.

Stofko-Hahn, R. E., Carr, D. W. and Scott, J. D. (1992). *FEBS lett.* 302, 274–278.

Török, K. and Trentham (1994) *Biochemistry* 33, 12807–12830.

VanEldick, L. J. and Lucas, T. J. (1987) *Meth. Enzymol.* 139, 393–405.

United Kingdom patent application "Isolation of enzymes" filed in the name of the Medical Research Council on Apr. 25th, 1996.

WO95/12672 Neri, D., Winter, G. P. and de Lalla, C.

What is claimed is:

1. A modified polypeptide ligand capable of binding a calcium dependent binding protein, which ligand comprises an amino acid sequence corresponding to that of a calcium dependent binding protein binding sequence of wild type ligand for the calcium dependent binding protein containing a substitution of at least one amino acid, which substitute amino acid has a hydrophobic side chain and substitutes into a helical peptide with minimal perturbation of the peptide structure, for a hydrophilic or aromatic amino acid, such that the affinity of the modified polypeptide ligand for the calcium dependent binding protein is enhanced, as determined by a reduction of the $K_d$ value or a reduction of the $k_{off}$ value, or both, relative to binding of the wild-type ligand to the calcium dependent binding protein.

2. The modified ligand according to claim 1, wherein the reduction of the $K_d$ or $K_{off}$ value is by a factor of at least 10.

3. The modified ligand according to claim 2, wherein the reduction of the $K_d$ or $k_{off}$ value is by a factor of at least 100.

4. The modified ligand according to claim 3, wherein the reduction of the $K_d$ or $k_{off}$ value is by a factor of at least 1000.

5. The modified ligand according to claim 1 in which the calcium dependent binding protein is calmodulin.

6. The modified ligand according to claim 1 in which the substitution is of a single amino acid in the wild type ligand sequence.

7. The modified ligand according to claim 1 in which the substitute hydrophobic amino acid is selected from the group consisting of alanine and valine.

8. The modified ligand according to claim 7 in which the substituted hydrophobic amino acid is alanine.

9. The modified ligand according to claim 1 in which the wild type ligand is selected from the group consisting of a myosin light chain kinase and a mastoparin.

10. The modified ligand according to claim 9 wherein the substitution is at one or more of positions 9, 14, or 20 in the sequence of myosin light chain kinase corresponding to SEQ ID NO: 7.

11. The modified ligand according to claim 9 in which the wild type ligand is mastaparan.

12. A molecule comprising i) the modified polypeptide ligand as described in claim 1, linked chemically to ii) another moiety selected from the group consisting of a substrate for a chemical reaction, a label, a toxin, and a targeting molecule.

13. The molecule according to claim 12, in which the targeting molecule is an antibody.

14. A method of enhancing the binding affinity of a polypeptide ligand capable of binding a calcium dependent binding protein, which method comprises substituting at least one hydrophilic or aromatic amino acid in an amino acid sequence corresponding to a calcium dependent binding protein binding sequence of a wild type ligand for the calcium dependent binding protein with a hydrophobic amino acid that substitutes into a helical peptide with minimal perturbation of the peptide structure, such that affinity of the polypeptide ligand for the calcium dependent binding protein is enhanced, as determined by a reduction of the $K_d$ value or a reduction of the $k_{off}$ value, or both, relative to binding of the wild type ligand to the calcium dependent binding protein.

15. The method of claim 14, wherein the reduction of the $K_d$ or $K_{off}$ value is by a factor of at least 10.

16. A binding pair comprising a calcium dependent binding protein and a molecule according to claim 12.

17. A method for binding two molecules, which method comprises contacting a molecule comprising a calcium dependent binding protein with a molecule comprising a modified ligand according to claim 1 under conditions that permit binding of the calcium dependent binding protein and the modified ligand.

18. The method of claim 17, wherein the molecules are in vivo.

19. The method of claim 17, wherein the molecules are immobilized.

* * * * *